United States Patent [19]

Toida et al.

[11] Patent Number: 4,550,240
[45] Date of Patent: Oct. 29, 1985

[54] LASER IRRADIATING APPARATUS

[75] Inventors: Masahiro Toida, Kanagawa; Norihiro Suenaga, Tokyo; Nobuyuki Suenaga, Kanagawa, all of Japan

[73] Assignee: Nippon Infrared Industries Co., Ltd., Tokyo, Japan

[21] Appl. No.: 445,186

[22] Filed: Nov. 29, 1982

[30] Foreign Application Priority Data

Sep. 21, 1982 [JP] Japan ................. 57-164338

[51] Int. Cl.⁴ ................................. B23K 26/00
[52] U.S. Cl. ................. 219/121 LS; 128/303.1; 128/4; 219/121 LU; 219/121 LV; 219/121 LN; 350/96.1
[58] Field of Search ............ 350/96.1, 96.26; 128/303.1, 395, 4, 6; 219/121 LS, 121 LP, 121 LQ, 121 LR, 121 LV, 121 LN, 121 LG

[56] References Cited

U.S. PATENT DOCUMENTS 3,710,798  1/1973  Bredemeier ............... 128/303.1
4,418,689 12/1983  Kanazawa .................. 128/6

Primary Examiner—C. L. Albritton
Attorney, Agent, or Firm—Cushman Darby & Cushman

[57] ABSTRACT

A laser irradiating apparatus comprising a first laser source for outputting a first laser beam, a second laser source for outputting a second laser beam, the laser beams being selectively irradiated through either a first light guide or a second light guide, a signal generating means for generating a first signal indicating use of the first light guide and a second signal indicating use of the second light guide; the first signal being generated when the said first light guide is used and the second signal being generated when the second light guide is used; a first assist gas supply means for supplying a first assist gas to the first light guide when the first signal is input; and a second assist gas supply means for supplying a second assist gas to the second light guide when the second signal is input.

11 Claims, 3 Drawing Figures

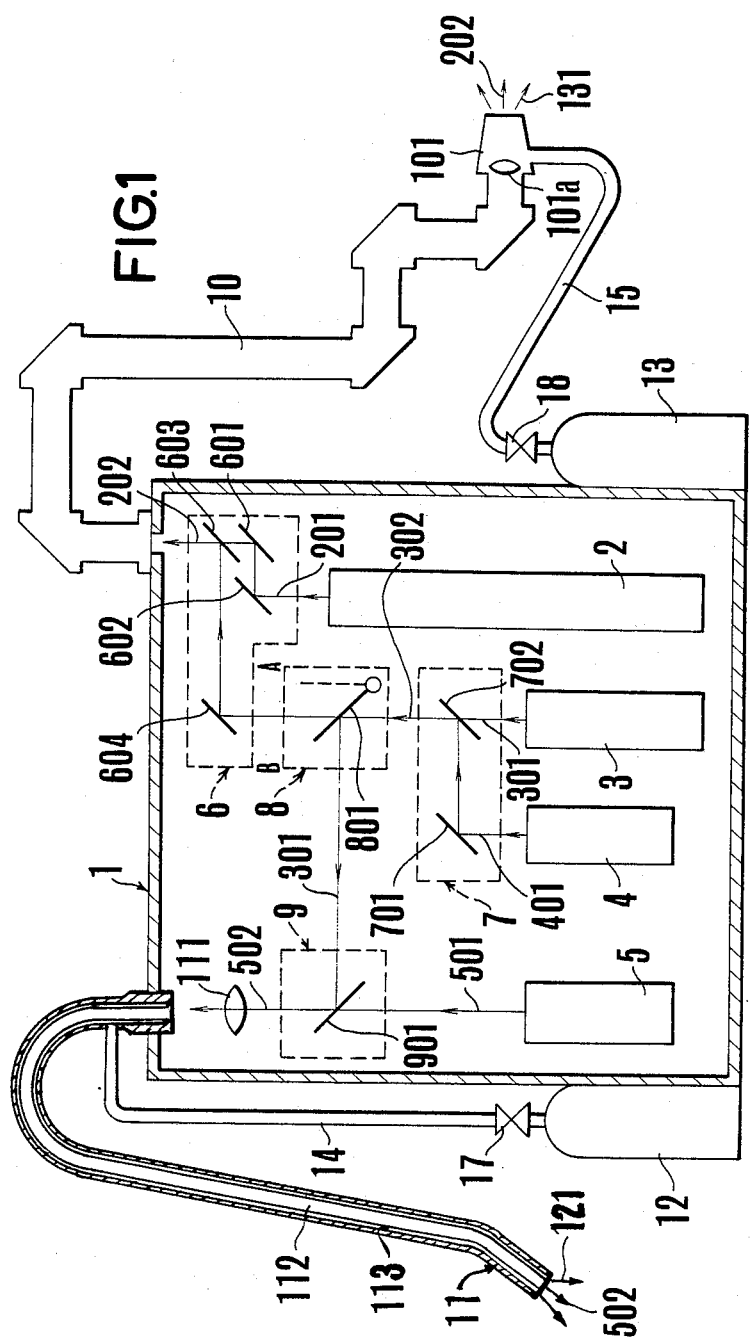

LASER IRRADIATING APPARATUS

BACKGROUND OF THE INVENTION

1. Field of the Invention

This invention relates to a laser irradiating apparatus, especially a laser irradiating apparatus for medical purposes, and more particularly a laser irradiating apparatus equipped with two pieces of laser light guides with different applicable fields.

2. Description of the Prior Art

As is well known, interaction between a living body and laser beam greatly depends upon the wavelength of the irradiation laser beam. So, appropriate irradiation of plural kinds of working laser beams with different wavelengths to affected parts of a living body enables much more effective and appropriate operations against given symptoms than that of a single laser beam only.

For instance, the use of YAG laser beams excellent in hemostasis and coagulation in combination with $CO_2$ laser beams excellent in incision acts to inhibit further hemorrhage during the operation. It is known that the same effect can be obtained when Ar laser beams are used in place of YAG laser beams.

Accordingly, conventionally some apparatus in which plural kinds of working laser beams with different wavelengths are simultaneously or optionally selected for irradiation have been proposed. For instance, as disclosed in the Japanese patent application Laid-Open No. 130145/81, an apparatus equipped with a $CO_2$ laser and a YAG laser, as working laser sources, and two pieces of laser light guides is known.

In this conventional apparatus, one of the laser light guides is a light guide for an articulated arm and irradiates $CO_2$ laser beams and YAG laser beams simultaneously or selectively. It goes without saying that this light guide is used for general surgical operations. Also, the other light guide is an optical fiber light guide and irradiates YAG laser beams only. This light guide is incorporated in an endoscope device and used for surgical operations under the endoscope visual field.

However, all the art apparatuses are concerned with the layout of the optical system and do not teach any practical consideration required when such apparatus are used for actual surgical operations.

SUMMARY OF THE INVENTION

The object of the present invention is the elimination of the above-mentioned shortcomings of the conventional laser irradiating apparatus. For this object, the present invention provides a laser irradiating apparatus equipped with two pieces of light guides with different applicable fields, in which some means to perform surgical operations smoothly such as injection of assist gas are automatically changed over according to a light guide to be used.

BRIEF DESCRIPTION OF THE DRAWINGS

FIG. 1 is a diagram illustrating one embodiment of the present invention.

FIG. 2b shows the operation of switches in the optical path change-over device of FIG. 2a.

DETAILED DESCRIPTION OF THE PREFERRED EMBODIMENT

Figure 2A:
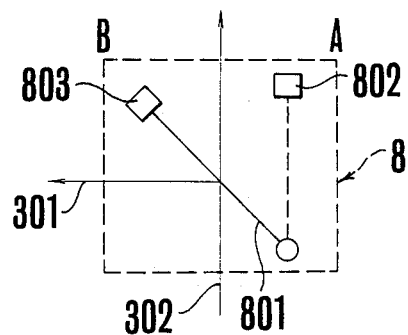
FIG. 2a shows an optical path change-over device used in the present invention.

The present invention will be described in detail with reference to the accompanying drawings. As shown in FIG. 1, the apparatus 1 of the present invention is provided with a first working laser source 2, a second working laser source 3, a first guide light source 4 and a second guide light source 5.

In the first working laser beam source 2, a $CO_2$ laser resonator which is excellent in incision capacity is used to output a first laser beam 201. On the other hand, in the second working laser beam source 3, a YAG laser resonator is used to output a second laser beam 301. Also, in the first guide light source 4, a He-Ne laser resonator is used to output a first guide red light 401. In the second guide light source 5, a halogen lamp is used to output a second guide white light 501.

Here, the second laser beam 301 and first guide light 401 are coaxially mixed by means of a second mixing means 7. As clearly shown, the mixing means 7 consists of a reflecting mirror 701 to reflect the first guide light 401, and a dichroic mirror 702 to transmit the second laser beam 301 and reflect the first guide light 401. Both beams adjusted coaxially by means of the mixing means 7 are output as a beam 302 as shown in the figure.

Also, the first laser beam 201 and the beam 302 are coaxially mixed by a mixing means 6. As shown in FIG. 1, the mixing means 6 consists of reflecting mirrors 601 and 602 to reflect the first laser beam 201, a reflecting mirror 604 to reflect the beam 302 and a dichroic mirror 603 to transmit the first laser beam 201 and reflect the beam 302. Both beams are adjusted coaxially by means of the mixing means 6 and are output as a beam 202 as shown in the FIG. 1.

The beam 202 is induced into an articulated arm light guide 10 to be irradiated to a desired target. The light guide 10 is used for general surgical operations. To the tip of the light guide 10, a handpiece 101 equipped with a condenser 101a is connected for condensing the beam 202.

To the handpiece 101, one end of a gas hose 15 is connected. To the other end of the hose 15, a first assist gas cylinder 13 is connected. A solenoid valve 18 is used to open or close a cylinder 13 in a state described later. When the solenoid valve 18 is opened, a first assist gas 131 is sent under pressure into the handpiece 101 and blown off through a tip opening. Though not illustrated, a pressure reducing valve is provided between the cylinder 13 and the solenoid valve 18 to reduce the gas 131 to an adequate pressure.

For the first assist gas 131, $N_2$ gas is used. As $CO_2$ gas absorbs the first laser beam 201 such as a $CO_2$ laser beam, etc., $CO_2$ gas is not desirable to use. Blowing off of the assist gas 131 prevents smoke, etc. occurring at the time of surgical operations from sticking to the condenser 101a and also conveniently cools the condenser 101a. When air is used in place of the $N_2$ gas, a compressor can be used instead of the cylinder.

On the other hand, an optical path change-over means 8 is provided on the optical path of the beam 302 to change over the beam optical path optionally. The means 8 changes over the optical path by making, for instance, the reflecting mirror 801 fixed to a rotary solenoid (not shown in the drawing) reflect the beam 302 or pass the beam 302 by. The means 8 is turned ON or OFF by the switch (not shown in the drawing) provided on the control panel so as to change over its set condition.

When the reflecting mirror 801 is at the A position, the beam 302 travels in straight lines and comes into the mixing means 6. When the reflecting mirror 801 is at the B position, the beam 302 optical path is changed over by the mirror and comes into a mixing means 9, which will be described later. Since the output of the first guide light 401 is prohibited, as described later, when the optical path is changed over, the second laser beam 301 comes into the mixing means 9.

The second laser beam 301 whose optical path has been changed over by the optical path change-over means 8 and the second guide light 501 from the second guide, light source 5 are coaxially mixed by means of the mixing means 9. The mixing means 9 consists of a dichroic mirror 901 to reflect, for instance, the second laser beam 301 and transmit the second guide light 501. Both beams are mixed coaxially and are output as a beam 502 as shown in the FIG. 1.

The beam 502 is induced into a fiber light guide 11. The fiber light guide 11 can irradiate the beam 502 to a desired target. The light guide 11 is incorporated in an endoscope device to apply it to surgical operations under an endoscope visual field.

The fiber light guide consists of an optical fiber 112 to guide the beam 502 and a jacketing tube 113 surrounding the fiber 112. There is a clearance provided between the fiber 112 and the jacketing tube 113, which forms a passage for the second assist gas as described later. The tip portion (injection end) of the jacketing tube 113 is, as the name implies, formed as an open end and the basic end is sealed.

The condenser 111 in the figure condenses the beam 502 when inducing the beam 502 into the fiber light guide 11. It goes without saying that the beam 502 condensed by the condenser 111 is induced into the optical fiber 112 and transferred thereby. Though not illustrated, a condenser may be provided at the tip of the fiber light guide 11 to condense the beams for irradiation.

One end of the gas hose 14 is connected to the jacketing tube basic end side. The other end of the hose 14 is connected to the second assist gas cylinder 12. A solenoid valve 17 in the figure opens or closes the cylinder 12 in a state described later. When the solenoid valve 17 is opened, the second assist gas 121 is sent under pressure into the jacketing tube and blown off through the fiber light guide tip portion. It goes without saying that the pressure of the gas 121 is reduced by a pressure reducing valve (not illustrated).

For the second assist which is 121, $CO_2$ gas harmless for a living body is used. Blowing off of the assist gas cools the optical fiber 112, and also prevents smoke generated at the time of surgical operations from sticking to the end surface of the optical fiber 112 and condenser (not illustrated).

With reference to FIG. 2, operative relations between the optical path change-over means 8 and the first guide light source 4, second guide light source 5 and solenoid valves 17 and 18 are described.

As shown in FIG. 2(a), the optical path change-over means 8 is equipped with limit switches 802 and 803, both of which are turned ON or OFF by a position, of the reflecting mirror 801. More specifically, when the reflecting mirror 801 is at the A position, the switch 802 is in the ON condition and the switch 803 is in the OFF condition. When the reflecting mirror 801 is at the B position, the switch 803 is in the ON position and the switch 802 is in OFF position. When the reflecting mirror 801 is driven by the rotary solenoid, both switches are turned ON or OFF by the rotary solenoid driving force.

Figure 2B:
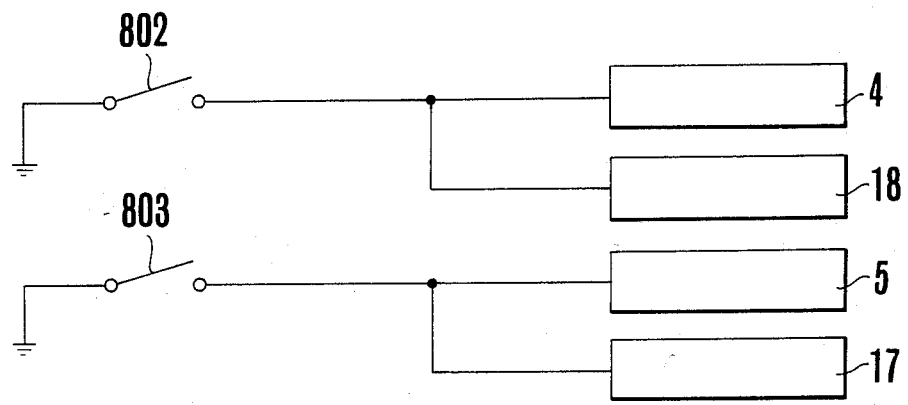

As shown in FIG. 2(b), the switch 802 is designed to control the first guide light source 4 and solenoid valve 18; when the reflecting mirror 801 is at the A position, the switch 802 becomes ON and thereby the first guide light source 4 and solenoid valve 18 are driven. Accordingly, the first guide light 401 is output from the first guide light source. Also, the solenoid valve 18 is opened to blow off the first assist gas 131 through the tip of handpiece 101 as previously described.

Likewise, the switch 803 is designed to control the second guide light source 5 and solenoid valve 17; when the reflecting mirror 801 is at the B position, the switch 803 turns ON and thereby the second guide light source 5 and solenoid valve 17 are driven. Accordingly, the second guide light 501 is output from the second guide light source 5. Also, the solenoid valves 17 is opened to blow off the second assist gas 121 through the tip of fiber light guide 11 as previously described.

When the reflecting mirror 801 is at the A position, the switch 803 is in the OFF position, the second guide light source 5 and solenoid valve 17 are not driven. Accordingly, the second guide light 501 is not output nor is the second assist gas 121 blown off. Likewise, when the reflecting mirror 801 is at the position, the switch 802 is in OFF condition and therefore the first guide light source 4 and solenoid valve 18 are not driven. Accordingly, the first guide light 401 is not output nor is the first assist gas 131 blown off.

According to a modification, a shutter is provided on each of the optical paths of the first guide light 401 and the second guide light 501, and these shutters are opened and closed by the signals from the switches 802 and 803, so as to control the outputs of the first guide light and the second guide light. In this case, needless to say, the first and second guide light sources 4 and 5 are kept in operation all the time.

As is evident from the foregoing description, the apparatus according to this invention is operated by the following modes.

(1) The first mode is obtained by setting the optical path change-over means 8 to the A position and driving the first working laser light source 2 and the second working laser light source 3. In the first mode, the first laser beam 201, the second laser beam 301 and the first guide light 401 are coaxially irradiated through the articulated arm light guide 10 and the first assist gas 131 is blown off.

(2) The second mode is obtained by setting the optical path change-over means 8 to the A position and driving the working laser beam 2 only, from among the two working laser beam sources. In the second mode, the first laser beam 201 and the first guide light 401 are coaxially irradiated from the articulated arm light guide 10 and the first assist gas 131 is blown off.

(3) The third mode is obtained by setting the optical path change-over means 8 to A position and driving the second working laser beam source 3 only from among the two working laser beam sources. In the third mode, the second laser beam 301 and the first guide light 401 are coaxially irradiated through the articulated arm light guide 10 and the first assist gas 131 is blown off.

(4) The fourth mode is obtained by setting the optical path change-over means 8 to B position and by driving the second working laser beam source 3 only, from among the two working laser beam sources. In the fourth mode, the second laser beam 301 and the second guide light 501 are coaxially irradiated through the fiber light guide 11 and the second assist gas 121 is blown off.

As described in detail in the foregoing, the apparatus according to the present invention is equipped with two kinds of light guides with different applicable fields and thereby is able to select adequately the light guide to be used according to the purposes. Especially, as the assist gas is automatically changed over according to the kind of the light guide to be used, the assist gas suitable for the surgical operating conditions can be used and is very convenient in practical application. For instance, $N_2$ gas and air, etc. which cause no inconvenience, such as absorption to the irradiating laser beam, can be used in the articulated arm light guide. In the fiber light guide, $CO_2$ gas, etc. which has no effect on the bio-tissue can be used. Moreover, when changed over to the light guide to be used, blowing-off of the assist gas from the light guide not in use is automatically stopped. Thus, this saves the operator's labor to stop blowing-off of the assist gas from the light guide not in use and is convenient.

In this way, the present invention is convenient both for surgical operations and for apparatus operations, and can provrde an excellent apparatus in practical operations.

In addition, if a respective different guide light is used according to the kind of the light guide to be used as shown in the embodiment, it will be more convenient in practical application, because the guide light in the fiber light guide uses a halogen lamp which is difficult to use in the articulated arm light guide. As the halogen lamp light has a high brightness and can be easily checked even in the bio-cavity, it is convenient when surgical operations are performed under an endoscope visual field.

When two pieces of guide light sources are not necessary in this apparatus, or a single guide light is used for both light guides, the second guide light source 5 can be omitted. In this case however, operation of both solenoid valves 17 and 18 remains unchanged.

It should be understood that the present invention is not limited to the foregoing embodiment, and many modified embodiments can be made within the scope of the present invention. For instance, even if the articulated arm light guide is replaced with a fiber light guide having transmission against the first laser beam, the same effect can be obtained. Also, when the first guide light source, the second guide light source and the two pieces of solenoid valves are controlled by a position of the reflecting mirror in the optical path change-over means, it is possible to design so that the first and second guide light sources and solenoid valves, etc. are driven only when desired, by treating signals from two pieces of switches provided in the means by means of an adequate logic circuit. Or, the first and second guide light sources and solenoid valves can be simultaneously switched ON or OFF by means of an outdoor switch to control the optical path change-over means instead of providing the position detecting switches. These matters apply to an apparatus in which a single guide light is used for two pieces of light guides.

What we claim:

1. A laser irradiating apparatus comprising a first laser source outputting a first laser beam, a second laser source outputting a second laser beam, said first beam being irradiated through a first light guide and said second laser beam being selectively irradiated through any one of said first light guide and a second light guide;

signal generating means for generating a first signal for indicating use of the first light guide and a second signal indicating use of the second light guide;

the first signal being generated when the first light guide is used and the second signal being generated when the second light guide is used;

first assist gas supply means for supplying a first assist gas to the first light guide when the first signal is input; and second assist gas supply means for supplying a second assist gas to the second light guide when the second signal is input.

2. A laser irradiating apparatus according to claim 1, further comprising:

optical path change-over means for selectively directing the second laser beam to any one of the first light guide and the second light guide; and mixing means for mixing the first laser beam and the second laser beam coaxially when said optical path change-over means directs said second laser beam to the first light guide.

3. A laser irradiating apparatus according to claim 2, wherein the signal generating means comprises a switch for detecting a setting state of the optical path change-over means.

4. A laser irradiating apparatus according to claim 2, wherein the signal generating means comprises an outside switch for turning ON or OFF the optical path change-over means.

5. A laser irradiating apparatus according to any of claims 1 to 4, which further comprises:

first storing means for storing the first assist gas, said means having an electromagnetic valve which is driven by the signal indicating the use of the first light guide to supply the first assist gas to the first light guide; and second storing means for storing the second assist gas, said means having an electromagnetic valve which is driven by the signal indicating the use of the second light guide to supply the second assist gas to the second light guide.

6. A laser irradiating apparatus according to claim 1 wherein the first light guide is an articulated arm light guide applicable to surgical operations, and the second light guide is a fiber light guide applicable to surgical treatment under an endoscope visual field.

7. A laser irradiating apparatus according to claim 1 wherein the first assist gas is $N_2$ gas and the second assist gas is $CO_2$ gas.

8. A laser irradiating apparatus according to claim 1 which further comprises:

a first guide light source for outputting a first guide light;

a second guide light source for outputting a second guide light;

whereby the output of the first guide light is allowed by the first signal indicating the use of the first light guide to supply the first guide light to the first light guide, and the output of the second guide light is allowed by the signal indicating the use of the second light guide to supply the second guide light to the second light guide.

9. A laser irradiating apparatus according to claim 8, wherein the first guide light source is He-Ne laser and the second guide light source is a halogen lamp.

10. A laser irradiating apparatus according to claim 1, wherein the first light guide is a fiber light guide applicable to surgical operations, and the second light guide is a fiber light guide applicable to surgical treatment under an endoscope visual field.

11. A laser irradiating apparatus according to claim 1, wherein the first assist gas is air and the second assist gas is $CO_2$ gas.

* * * * *